United States Patent
Ginn

(10) Patent No.: US 7,393,363 B2
(45) Date of Patent: *Jul. 1, 2008

(54) LUNG ASSIST APPARATUS AND METHODS FOR USE

(75) Inventor: Richard S. Ginn, San Jose, CA (US)

(73) Assignee: Gateway Medical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/421,004

(22) Filed: May 30, 2006

(65) Prior Publication Data

US 2006/0247792 A1 Nov. 2, 2006

Related U.S. Application Data

(60) Continuation of application No. 11/016,409, filed on Dec. 17, 2004, now Pat. No. 7,112,225, which is a continuation of application No. 10/750,800, filed on Jan. 2, 2004, now Pat. No. 6,837,906, which is a division of application No. 09/922,344, filed on Aug. 3, 2001, now Pat. No. 6,743,259.

(51) Int. Cl.
*A61F 2/04* (2006.01)
(52) U.S. Cl. .................................. 623/23.64
(58) Field of Classification Search .............. 623/23.64, 623/23.65, 23.68, 1.31, 1.35
See application file for complete search history.

(56) References Cited

U.S. PATENT DOCUMENTS

| | | | |
|---|---|---|---|
| 3,683,655 A | 8/1972 | White et al. | |
| 3,757,783 A | 9/1973 | Alley | |
| 5,306,234 A | 4/1994 | Johnson | |
| 5,588,424 A | 12/1996 | Insler et al. | |
| 5,588,992 A | 12/1996 | Scott et al. | |
| 5,707,352 A | 1/1998 | Sekins et al. | |
| 5,782,905 A * | 7/1998 | Richter | 623/1.1 |
| 5,855,601 A | 1/1999 | Bessler et al. | |
| 5,904,648 A | 5/1999 | Arndt et al. | |
| 5,954,636 A | 9/1999 | Schwartz et al. | |

(Continued)

OTHER PUBLICATIONS

Clifton A. Alferness, et al., EPO Publication No. EP 1 078 601 A2, "Lung Volume Reduction Apparatus", Feb. 28, 2001.

(Continued)

*Primary Examiner*—Bruce E. Snow
(74) *Attorney, Agent, or Firm*—Orrick, Herrington & Sutcliffe LLP

(57) ABSTRACT

A lung-assist apparatus includes a tubular housing, a tubular nozzle therein, and a first valve disposed between the housing and nozzle. The housing is implanted across a bifurcation such that the nozzle extends from a first branch communicating with a healthy region of a lung towards a main passage, and terminates proximate a lateral opening in the housing that is disposed within a second branch communicating with a damaged region of the lung. During inhalation, the first valve opens to allow air flow into the first branch, and closes during exhalation to force air through the nozzle, thereby inducing a vacuum for drawing air from the damaged region. A second valve in the second branch opens during exhalation to draw air from the diseased region, and closes during inhalation to prevent air from being drawn into the damaged region.

3 Claims, 5 Drawing Sheets

U.S. PATENT DOCUMENTS

| | | |
|---|---|---|
| 6,003,517 A | 12/1999 | Sheffield et al. |
| 6,020,380 A | 2/2000 | Killian |
| 6,027,525 A | 2/2000 | Suh et al. |
| 6,174,323 B1 | 1/2001 | Biggs et al. |
| 6,258,100 B1 | 7/2001 | Alferness et al. |
| 6,327,505 B1 | 12/2001 | Medhkour et al. |
| 6,645,242 B1 * | 11/2003 | Quinn ................. 623/1.16 |
| 2001/0037808 A1 | 11/2001 | Deem et al. |
| 2001/0052344 A1 | 12/2001 | Doshi |
| 2002/0112729 A1 | 8/2002 | DeVore et al. |

OTHER PUBLICATIONS

T. Sabanathan, PCT Publication No. WO 98/48706, "Occlusion Device", Nov. 5, 1998.

C. Danek, et al., PCT Publication No. WO 00/62699, "Modification of Airways by Application of Energy", Oct. 26, 2000.

Rodney A. Perkins, et al., PCT Publication No. WO 01/02042 A1, "Methods, Systems, and Kits for Lung Volume Reduction", Jan. 11, 2001.

Clifton A. Alferness, et al., PCT Publication No. WO 01/13839 Amendment, Lung Reduction Device, System, and Method, Mar. 1, 2001.

Edward P. Ingenito, PCT Publication No. WO 01/13908 A2, "Tissue Volume Reduction", Mar. 1, 2001.

* cited by examiner

LUNG ASSIST APPARATUS AND METHODS FOR USE

RELATED INFORMATION

This application is a continuation of application Ser. No. 11/016,409 filed Dec. 17, 2004, which issued as U.S. Pat. No. 7,112,225, on Sep. 26, 2006, which is a continuation of application Ser. No. 10/750,800 filed on Jan. 2, 2004, which issued as U.S. Pat. No. 6,837,906 on Jan. 4, 2005, which is a divisional of application Ser. No. 09/922,344 filed on Aug. 3, 2001, which issued as U.S. Pat. No. 6,743,259 on Jun. 1, 2004. The priority of the prior application is expressly claimed, and the disclosure of this application is hereby incorporated by reference in its entirety.

FIELD OF THE INVENTION

The present invention relates generally to apparatus and methods for treating chronic occlusive pulmonary disease, and more particularly to apparatus and methods for enhancing or assisting breathing, particularly exhalation from one or more regions of a lung using exhalation from a healthier region of the lung.

BACKGROUND

Patients with chronic bronchitis or other chronic occlusive pulmonary disease ("COPD") may have reduced lung capacity and/or efficiency due to lung tissue breaking down. For example, in severe chronic pulmonary disease, e.g., emphysema, lung tissue may be damaged or destroyed, reducing the ability of the lung to effectively transfer oxygen. One of the problems with emphysema and like conditions is that the lungs become over-inflated, filling the chest cavity and preventing the patient from being able to inhale effectively.

In severe emphysema cases, lung volume reduction surgery ("LVRS") has been suggested to improve lung efficiency. LVRS is performed by opening the chest cavity, retracting the ribs, and stapling off and removing a diseased or partially diseased portion of a lung. This may allow the remaining healthier lung tissue to inflate more fully within the chest cavity, thereby increasing lung efficiency. LVRS, however, is an extremely invasive procedure, and exposes the patient to substantial post-operative complications.

Accordingly, apparatus and methods for assisting breathing in patients having COPD and like conditions, possibly avoiding the need for open surgery, would be considered useful.

SUMMARY OF THE INVENTION

The present invention is directed to apparatus and methods for treating chronic occlusive pulmonary disease, and particularly to lung assist apparatus and to methods for using such apparatus to enhance and/or assist breathing, particularly exhalation from one or more regions of a lung. Preferably, the apparatus and methods of the present invention use air flowing from a healthy region of a lung to assist exhalation of air from a damaged or diseased region of the lung.

In accordance with a first aspect of the present invention, an apparatus is provided that includes a support structure that is implantable within a branch between a main passage and first and second branches. The support structure includes a first end, a second end, and a lateral opening therebetween. The support structure may be expandable between a contracted condition for facilitating insertion into the lung, and an enlarged condition for implantation proximate the branch. For example, the support structure may include a tubular mesh, possibly including engagement elements, such as barbs, for engaging tissue surrounding the branch.

A tubular member, e.g., a nozzle, including an inlet end, an outlet end, and an inner lumen and an outer surface extending therebetween, may be carried by the support structure such that the inlet end is disposed proximate the first end, and the outlet end is disposed proximate the lateral opening. The apparatus preferably defines an outer lumen between the outer surface of the nozzle and the support structure. A first valve may be disposed across the outer lumen for controlling flow through the outer lumen in a predetermined manner. Preferably, the first valve is configured for permitting flow through the outer lumen towards the inlet end and/or for limiting flow through the outer lumen towards the outlet end. More preferably, the first valve is configured to close to prevent substantial air flow through the outer lumen towards the second end of the support structure, and cause air to pass through the inner lumen in order to exit out the second end, thereby generating a vacuum at the lateral opening.

Optionally, the apparatus may include a second valve for limiting flow into or out of the lateral opening of the support structure. Preferably, the second valve is configured to open when a vacuum is generated in the lateral opening to allow air flow into the lateral opening towards the second end of the support structure. More preferably, the second valve is also configured to close when a vacuum is absent from the lateral opening, thereby preventing substantial air flow out of the lateral opening.

The nozzle, first valve, and/or second valve may be substantially permanently attached to the support structure, e.g., by struts. Alternatively, one or more of the components may be attachable to the support structure. In a further alternative, one or more of the components may be implanted independently within a lung proximate a branch, e.g., a bifurcation, such that, optionally, the support structure may even be eliminated.

Preferably, the first end of the support structure in its enlarged condition and the outlet end of the nozzle have a predetermined relative cross-section for generating a predetermined vacuum in the lateral opening when air passes through the inner lumen and out the outlet end. The predetermined vacuum may be selected to induce a desired flow rate into the lateral opening, e.g., from a diseased or damaged region of a lung, as described further below.

In accordance with another aspect of the present invention, a method is provided for assisting air flow through a branch in a lung. Generally, the branch includes a main passage, e.g., a bronchus or bronchiole, a first branch communicating with a healthy region of the lung, and a second branch communicating with a region of the lung to be at least partially isolated. The isolated region may be a diseased or damaged region, e.g., including diseased and/or damaged tissue (although the region may also include at least some healthy tissue).

Initially, a nozzle device may be provided that includes a nozzle or other tubular member including an inlet end, an outlet end, and an inner lumen and an outer surface extending therebetween. The nozzle device may also include a first valve disposed adjacent the outer surface, the first valve being configured to close and/or limit flow along the outer surface from the inlet end towards the outlet end. Preferably, the first valve is configured to open for allowing flow along the outer surface from the outlet end towards the inlet end and to close for restricting or preventing substantial flow along the outer surface from the outlet end to the inlet end, as described above.

The nozzle device may be implanted in the branch such that the inlet end is disposed in the first branch, and the outlet end is disposed proximate the second branch. Preferably, the first valve closes during exhalation to force air from the first branch to pass through the inner lumen into the main passage, thereby inducing a vacuum at the second branch for drawing air from the damaged region into the main passage. During inhalation, the first valve preferably opens to allow substantially unlimited flow into the first branch from the main passage.

A second valve may be implanted in the second branch, the second valve configured to open during exhalation to allow air to be drawn from the isolated region into the main passage, and configured to close during inhalation to prevent air from being drawn into the isolated region.

In one method, a support structure may be implanted within the branch. For example, the support structure may include a tubular mesh that is expandable between a contracted condition for facilitating delivery into a lung, and an enlarged condition for engaging tissue at the branch. After implantation of the support structure, the device may be introduced and secured to the support structure, e.g., by struts extending from one of the nozzle device and the support structure and cooperating slots, detents, or other connectors on the other of the nozzle device and the support structure.

Alternatively, the nozzle device may include a support structure to which the nozzle, first valve, and/or second valve are substantially permanently attached. Thus, the entire nozzle device may implanted in one step, e.g., by securing the support structure to tissue at the branch.

Other objects and features of the present invention will become apparent from consideration of the following description taken in conjunction with the accompanying drawings.

DETAILED DESCRIPTION OF THE PREFERRED EMBODIMENTS

Figure 1:
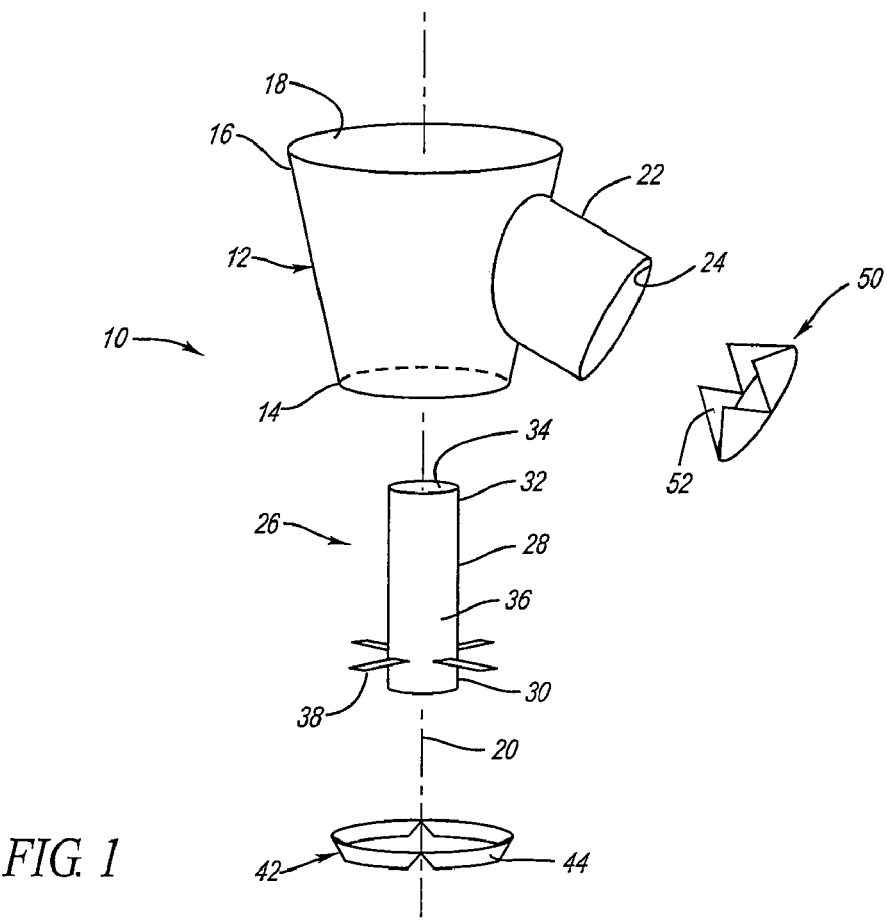
FIG. 1 is an exploded side view of a first preferred embodiment of an apparatus for assisting lung exhalation, in accordance with the present invention.

Turning now to the drawings, FIG. 1 shows a first preferred embodiment of a lung assist apparatus 10, in accordance with the present invention. Generally, the apparatus 10 includes a housing 12 or other support structure, a nozzle 26 disposed within at least a portion of the housing 12, and a first valve 42 disposed between the nozzle 26 and the housing 12. Preferably, the apparatus 10 also includes a second valve 50 that may control flow through a lateral opening 24 in the housing 12, as described further below. The components of the apparatus 10 are preferably attached to the housing 12, thereby providing a single deliverable device, although alternatively one or more of the components may be provided separately from the housing 12 and implanted in stages, as described further below.

The housing 12 includes a first end 14, a second end 16, and a lumen 18 therebetween, thereby defining a longitudinal axis 20. In a preferred embodiment, the housing 12 is a tubular body, e.g., formed from a plurality of rings (not shown) connected to one another. Preferably, to enhance flexibility and/or conformability, the housing 12 may include a plurality of holes (not shown) therethrough, thereby defining a tubular mesh structure. For some applications, a mesh structure may also be preferred to promote endothelialization or other tissue ingrowth through the wall of the housing 12. For example, mesh structures, similar to those used for stents or other endoprostheses, may be appropriate for use as a housing 12 in accordance with the present invention, such as that shown in FIGS. 6A and 6B.

The housing 12 may be tapered, as shown, in order to facilitate implantation of the apparatus 10 within a tapered branch between a main passage and first and second branches, as shown in FIGS. 4A-4D, and described further below. Alternatively, the housing 12 may have a substantially uniform diameter or cross-section (not shown) between the first and second ends 14, 16. A uniform cross-section may be appropriate for branches that are substantially uniform in cross-section, or if the housing 12 is sufficiently conformable to line or otherwise securely affix to tissue defining the wall(s) of a tapered branch.

In addition, barbs or other tissue engaging elements (not shown) may be provided that extend from the housing 12, e.g., from the first and second ends 14, 16, to further enhance engagement with the wall(s) of a branch. An adhesive (not shown) may be provided on one or more regions of the housing 12, e.g., on the outside of the first and second ends 14, 16, in addition to or instead of the tissue engaging elements.

The housing 12 may be radially compressible to a contracted condition for facilitating insertion into a lung, e.g., through a trachea, bronchus, bronchiole, and/or other bronchial passage, and radially expandable to an enlarged condition for implantation within the branch. In a preferred embodiment, the housing 12 is formed from a superelastic and/or shape memory material, such as Nitinol, such that the housing 12 is resiliently compressible to the contracted condition, yet is biased to expand towards the enlarged condition. Alternatively, the housing 12 may be plastically deformable between the contracted and enlarged conditions.

The housing 12 includes a leg 22 defining the lateral opening 24 that communicates with the lumen 18. Alternatively, the lateral opening 24 may be provided directly in a wall of the housing 12 without the leg (not shown), which may reduce the profile of the apparatus 10, e.g., when compressed towards the contracted condition for delivery.

In alternative embodiments, it may be possible to eliminate the housing 12 or to provide an elongate rail, frame, or other support structure (not shown) for securing individual or multiple components of the apparatus 10 within a branch, as described further below.

Figure 2:
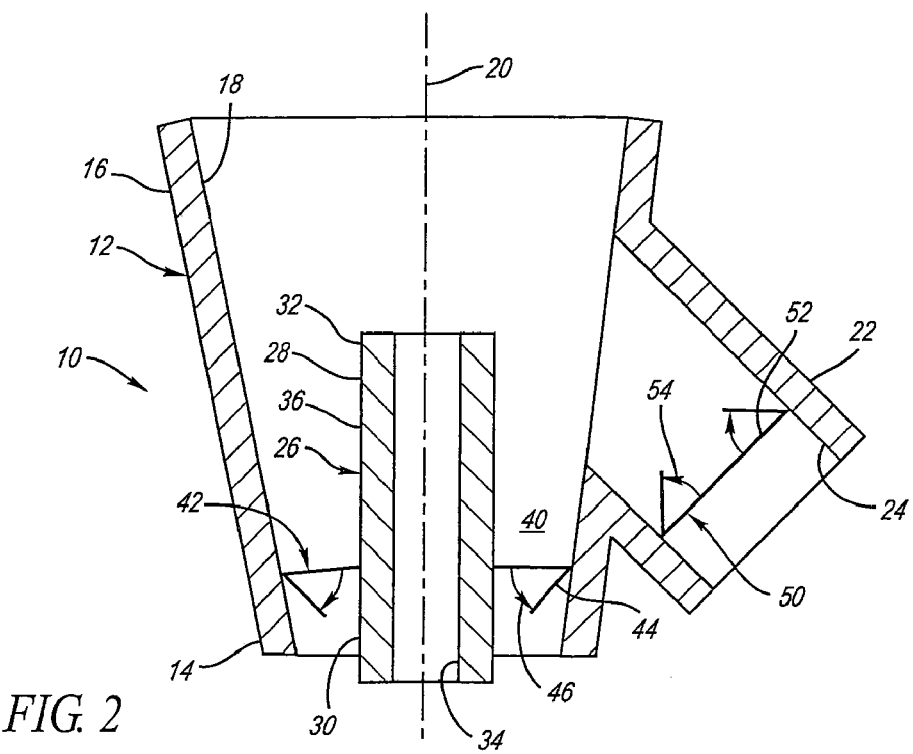
FIG. 2 is a cross-sectional side view of the apparatus of FIG. 1.

With further reference to FIGS. 1 and 2, the nozzle 26 generally includes a tubular member 28, including an inlet end 30, an outlet end 32, and an inner lumen 34. The tubular member 28 has a solid wall defining an outer surface 36 and openings in the inlet and outlet ends 30, 32. The tubular member 28 may have a substantially uniform diameter or cross-section, as shown, or alternatively may be tapered in a desired manner.

The nozzle 26 may include one or more struts 38 or other elements allowing attachment to the housing 12 such that an outer lumen 40 is defined between the outer surface 36 of the nozzle 26 and the inside of the housing 12. The struts 38 may be substantially permanently attached to the housing 12 such that the nozzle 26 and the housing 12 define a unitary assembly. Alternatively, the struts 38 may include tabs, detents, or other connectors (not shown) that may be received in slots, pockets, or other mating connectors (also not shown) in the wall of the housing 12, e.g., if the nozzle 26 is removably attachable to the housing 12.

Preferably, the nozzle 26 is carried by the housing 12 such that the inlet end 30 is disposed adjacent the first end 14, and the outlet end 32 is disposed proximate the lateral opening 24. Although the nozzle 26 is preferably concentrically disposed within the housing 12, as shown, the nozzle 26 may be arranged asymmetrically within the housing 12, e.g., against a wall of the housing 12, if desired. Preferably, the housing 12 and nozzle 26 have a predetermined cross-sectional ratio, i.e., between the cross-sectional area of the first end 14 of the housing 12 in its enlarged condition, and the cross-sectional area of the inner lumen 34, as explained further below.

The first valve 42 is disposed across the outer lumen 40, e.g., connected to the nozzle 26 and/or housing 12, to control flow through the outer lumen 40. Preferably, the first valve 42 is configured for permitting flow through the outer lumen 40 towards the first end 14 of the housing and for limiting flow through the outer lumen 40 towards the second end 16. For example, the first valve 42 may include a plurality of leaflets 44 or other known valve mechanism. The leaflets 44 may open towards the first end 14 (as designated by arrows 46, shown in phantom) to allow free flow through the outer lumen 40 towards the first end 14, yet may close to seal the outer lumen 40 and prevent substantial flow towards the second end 16.

Thus, if flow is directed through the housing 12 from the second end 16 towards the first end 14, the first valve 42 may open and allow air (or other fluid) to flow freely and substantially unobstructed through the housing 12. In contrast, if flow is directed through the housing 12 from the first end 14 towards the second end 16, the first valve 42 may close, thereby causing any air to pass through the inner lumen 34 and out the outlet end 32 of the nozzle 26. Because of the reduced cross-section of the inner lumen 34 as compared to the cross-section of the first end 14 of the housing 12 in the enlarged condition, the velocity of flow through the inner lumen 34 and out the outlet end 32 may be increased substantially, as compared to the velocity of air entering the first end 14 of the housing 12. As will be appreciated by those skilled in the art, pursuant to Bernoulli's law of fluid mechanics, this increase in velocity at the outlet end 32 of the nozzle 26 may create a reduction in pressure in the leg 22 (i.e., may generate a vacuum), thereby drawing additional air into the lateral opening 24 and through the second end 16 of the housing 12.

Optionally, the second valve 50 may be provided within or proximate the leg 22 to limit or otherwise control flow through the lateral opening 24. For example, the second valve 50 may include a plurality of leaflets 52 that open (as designated by arrows 54, shown in phantom) to allow air flow into the lateral opening 24 (towards the second end 16 of the housing 12), while limiting flow out of the lateral opening 24. Preferably, the leaflets 52 close to seal and prevent substantial air flow out of the lateral opening 24, as described further below.

Turning to FIGS. 3 and 4A-4C, implantation and use of the lung-assist apparatus 10 is shown. First, a lung assist apparatus 10 is provided, similar to that described above, that includes a housing 12, a nozzle 26 attached therein, and first and second valves 42, 50. The housing 12 may be compressed towards a contracted or delivery condition to facilitate introduction into a patient's lung. For example, the housing 12 may be compressed radially inwardly, e.g., towards the nozzle 26, which may compress the leg 22. Alternatively, the housing 12 may be twisted about the longitudinal axis 20 relative to the nozzle 26 to reduce the cross-section of the housing 12. Consequently, the struts 38 may be wrapped at least partially around the nozzle 26 and/or the leaflets 44 of the first valve 42 may be compressed against the outer surface 36 of the nozzle 26.

Figure 3:
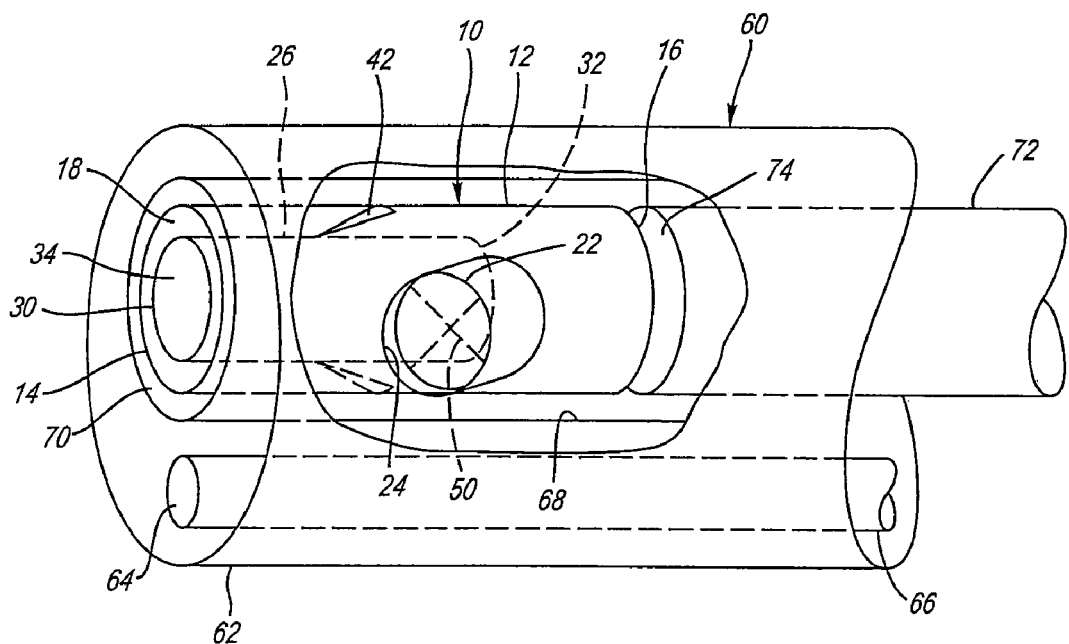
FIG. 3 is a perspective view, with a partial cut-away, of a delivery apparatus for delivering the lung assist apparatus of FIGS. 1 and 2 into a patient's lung.

Turning to FIG. 3, the apparatus 10 may be constrained in the contracted condition, e.g., by compressing the housing 12, as described above, and inserting the apparatus 10 into a distal end 62 of a delivery apparatus 60. The delivery apparatus 60 may be a bronchoscope, e.g., including a lens 64, a fiber optic filament 66, a camera (not shown) optically coupled to the lens 64, and/or a light (also not shown) on the distal end 62. Alternatively, other tubular members may be provided, e.g., including a lumen 68 extending between the proximal end (not shown) and the distal end 62. The apparatus 10 may be slidably inserted into a distal portion 70 of the lumen 68 adjacent the distal end 62. The delivery apparatus 60 may also include a plunger or other stop member 72 disposed within the lumen 64 that includes a substantially blunt distal end 74 adjacent the apparatus 10. Thus, the lung assist apparatus 10 may be "pushed" out of the lumen 64, e.g., by retracting the bronchoscope or outer tubular member while holding the stop member 72 in position, and/or by directing the stop member 72 distally relative to the bronchoscope 60.

Alternatively, the delivery apparatus may be a tubular sheath including one or more filaments or other elements (not shown) that may be wrapped around and/or threaded through the apparatus 10 to constrain the apparatus 10, e.g., to constrain the housing 12 in the contracted condition and/or to secure the apparatus 10 to an outer surface of the sheath (not shown).

Figure 4A:
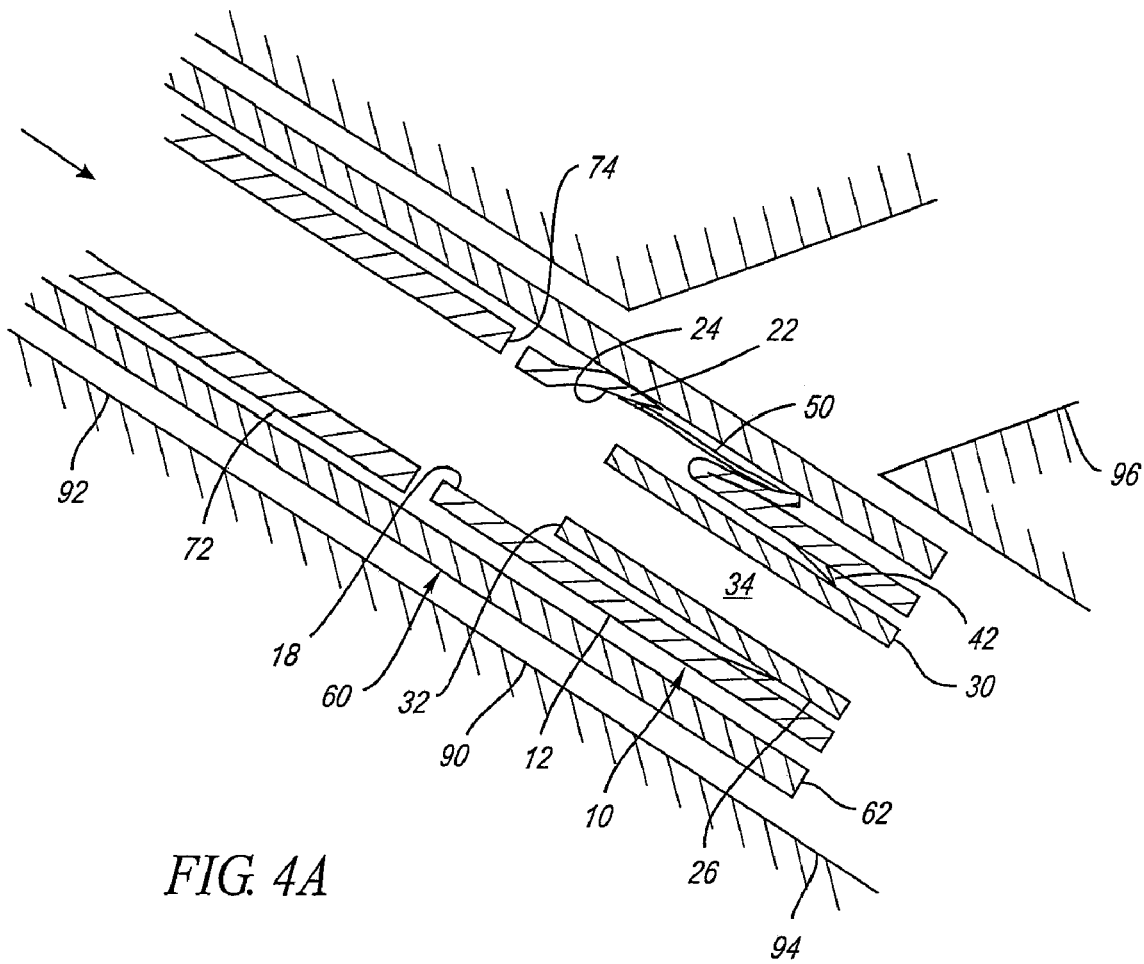
FIGS. 4A-4C are cross-sectional views of a bifurcation within a lung, showing a method for implanting a lung assist apparatus, in accordance with the present invention.
Figure 4B:
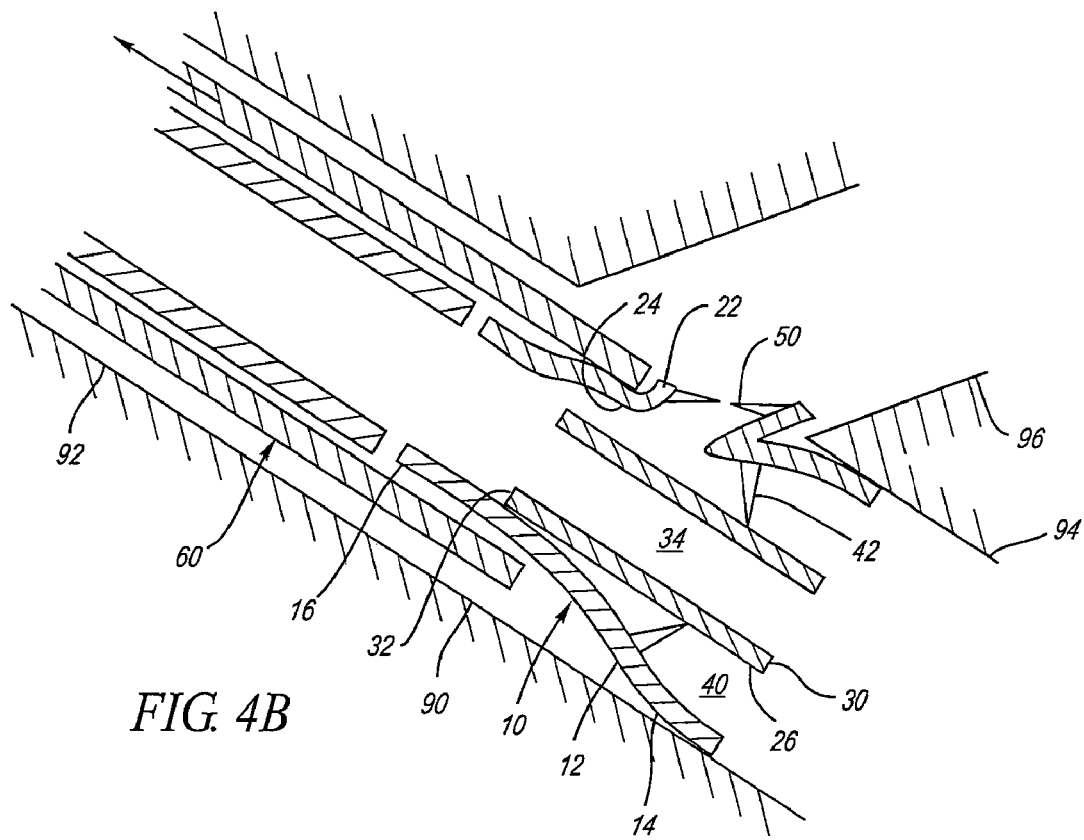
Figure 4C:
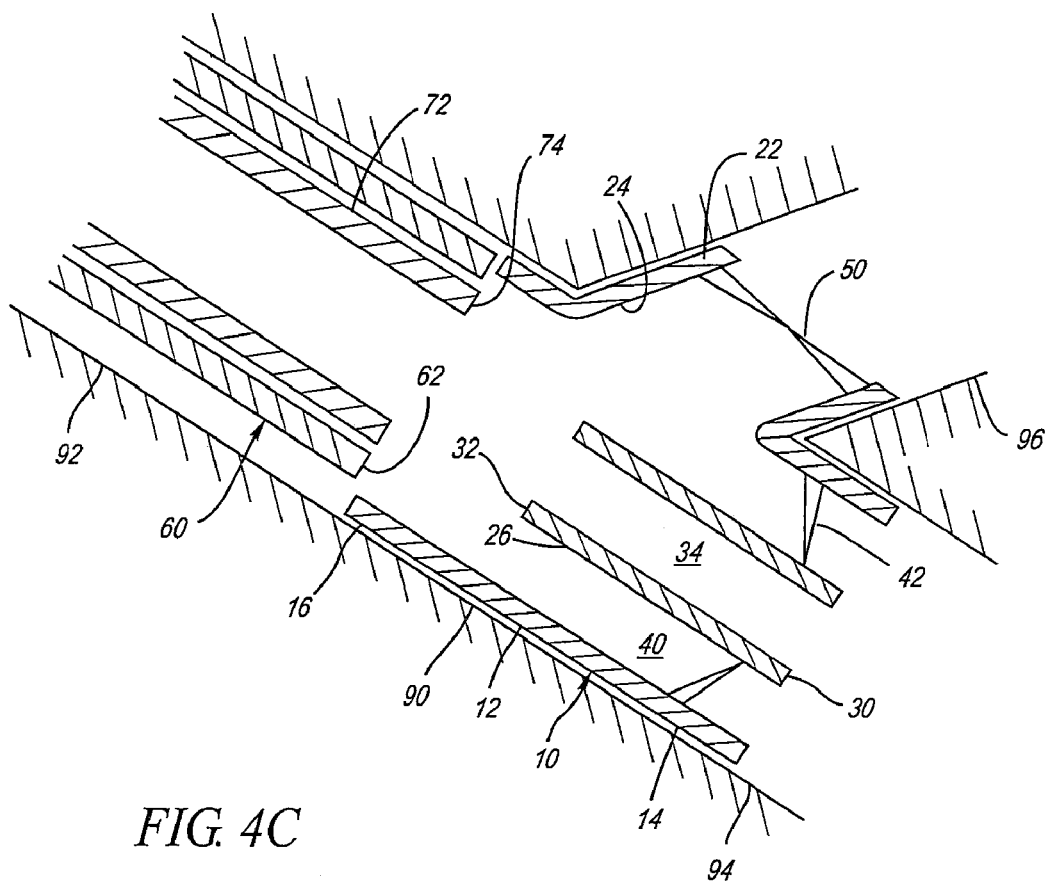

Turning to FIGS. 4A-4C, the distal end 62 of the delivery apparatus 60 may be introduced into a patient, e.g., and advanced via the trachea into a bronchus, bronchiole, or other bronchial passage (not shown). Using the lens 64, a camera or other imaging device (see FIG. 3, not shown in FIGS. 4A-4D for simplicity) on the delivery apparatus 60 (or optionally, using a separate bronchoscope, also not shown), the distal end 62 of the delivery apparatus 60 may be introduced into the bronchial passage. Preferably, the distal end 62 is extended across a target branch, e.g., a bifurcation 90 between a main passage 92 across to a first branch 94, as shown in FIG. 4A. The first branch 94 preferably communicates with a relatively healthy region of the lung (not shown). The bifurcation 90 also includes a second branch 96, extending substantially laterally relative to the main passage 92. The second branch 96 preferably communicates with a region to be isolated, e.g., a damaged and/or diseased region of a lung (not shown), i.e., including a substantial amount of tissue damaged by emphysema or other occlusive pulmonary disease.

The delivery apparatus 60 may be positioned such that the first and second ends 14, 16 of the housing 12 are disposed on either side of the second branch 96. In addition or alternatively, if necessary, the delivery apparatus 60 may be rotated about longitudinal axis 20 to align the lateral opening 24 of the housing 12 with the second branch 96, as shown in FIG. 4A. Both of these positioning aspects may be observed using direct visualization, e.g., using a bronchoscope, and/or using external imaging, such as fluoroscopy (not shown). If fluoroscopy is used, the housing 12 may include one or more radiopaque markers (not shown) for identifying the axial location and/or radial orientation of the housing 12.

Once properly positioned, the apparatus 10 may be deployed from the delivery apparatus 60, e.g., by withdrawing the delivery sheath 60, while restraining the apparatus 10 from proximal movement using the stop member 72, as shown in FIG. 4B. In addition or alternatively, the stop member 72 may be advanced distally during deployment, e.g., to direct the housing 12 into position and/or to direct the lateral opening 24 into the second branch 96, as shown in FIG. 4C.

Preferably, as the apparatus 10 is deployed, the housing 12 automatically expands towards the enlarged condition, thereby substantially engaging tissue surrounding the bifurcation 90, e.g., tissue within the main passage 92 and the first branch 94. Alternatively, the housing 12 may be plastically expanded, e.g., by mounting the housing 12 on a balloon catheter or other expandable device (not shown). In this alternative, the apparatus 10 may be exposed, e.g., by retracting an overlying sheath, or filaments (not shown) may be removed, and a balloon underlying the housing 12 may be expanded to expand the housing 12 towards the enlarged condition.

Figure 5A:
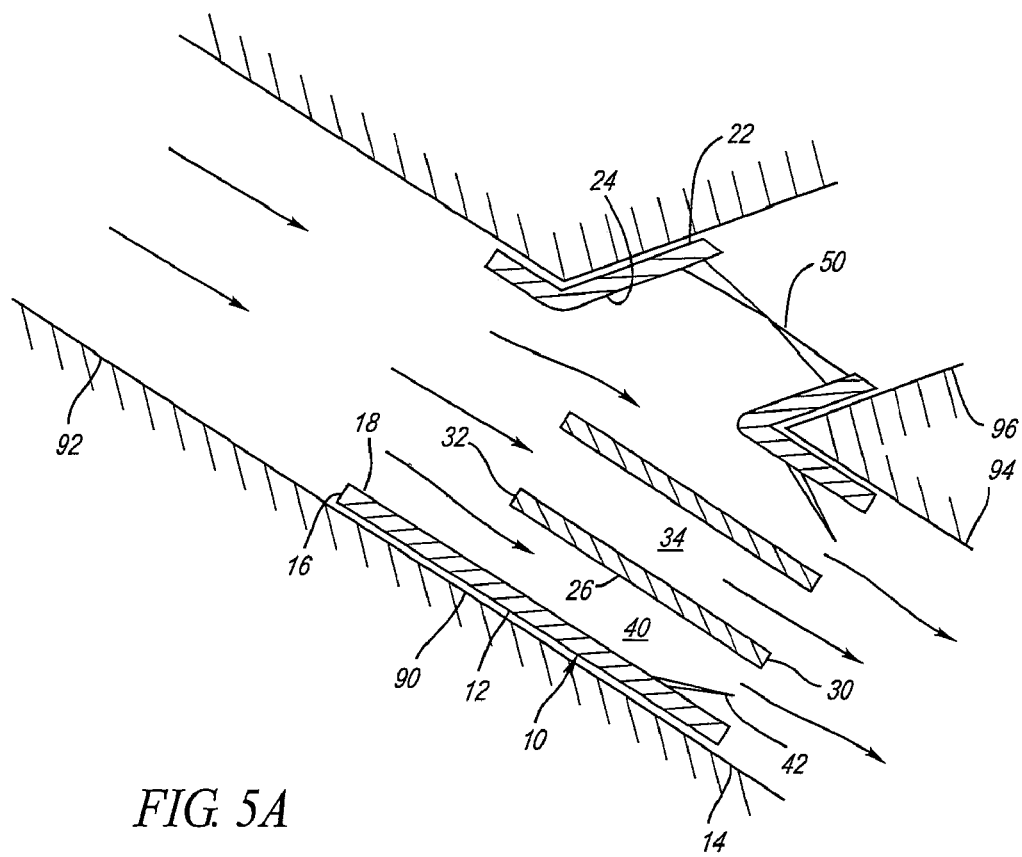
FIGS. 5A and 5B are cross-sectional side views of a lung-assist apparatus implanted within a bifurcation, showing air flow during inhalation and exhalation, respectively.
Figure 5B:
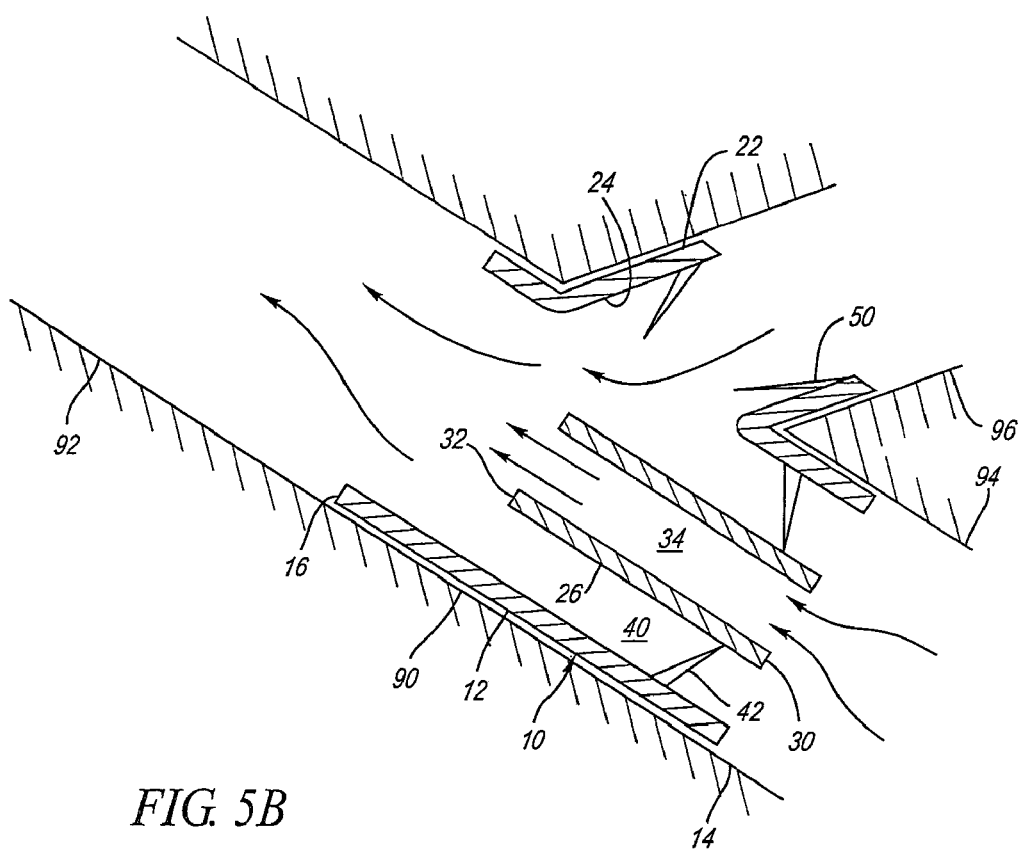

Turning to FIGS. 5A and 5B, the delivery apparatus 60 may be removed (not shown), leaving the apparatus 10 implanted within the bifurcation 90 to assist during breathing. Preferably, the nozzle 26 is disposed such that the inlet end 30 is disposed towards the first branch 94, the outlet end 32 is directed towards the main passage 92, and the lateral opening 24 extends into the second branch 96, as shown. Thus, the first end 14 of the housing 12 may be directed towards a healthy region of a lung and the lateral opening 24 may be directed towards a diseased or damaged region, or other region from which evacuation assistance is desired.

As shown in FIG. 5A, during normal inhalation, the first valve 42 may open, allowing air to flow freely from the patient's trachea into the healthy region of lung via the first branch 94. Substantially simultaneously, the second valve 50 may close, because of the absence of a vacuum at the lateral opening 24, preventing substantial air flow into the diseased region of the lung via the second branch 96 and effectively isolating the diseased region. Thus, air may be free to flow from the second end 16 of the housing 12 through the entire lumen 18 (including the inner lumen 34 and the outer lumen 40) to the first end 14 of the housing 12, while air flow is prevented out the lateral opening 24 into the isolated diseased region.

Conversely, as shown in FIG. 5B, during normal exhalation, the first valve 42 may be biased to close, preventing air from flowing through the outer lumen 40. With the first valve 42 closed, any air flowing through the apparatus 10 must necessarily flow through the inner lumen 34 of the nozzle 26. Because of the reduced cross-section of the inner lumen 34 relative to the entire lumen 18, the velocity of the air flowing through the nozzle 26 may substantially increase. According to Bernoulli's Law, the increase in velocity is directly proportional to the ratio of the cross-sectional areas of the lumen 18 at the first end 14 and the inner lumen 34. This increase in velocity may create a vacuum at the lateral opening 24 sufficient to cause the second valve 50 to open. Consequently, the vacuum may draw air from the second branch 96, and consequently from the diseased region of the lung communicating with the second branch 96.

The amount of vacuum generated by the apparatus 10 may be easily determined, as will be appreciated by those skilled in the art. Given the cross-sectional area of the first branch 94, the main passage 92, and/or the second branch 96, an apparatus 10 may be selected that has a housing 12 with an enlarged condition that may effectively secure the apparatus 10 within the target bifurcation 90. An appropriate nozzle 26 may be selected having an inner lumen 34 defining a predetermined cross-sectional area relative to the housing 12 in its enlarged condition. The first and second valves 42, 50 may be selected such that they may be biased to open and/or close at predetermined pressures to enable operation of the apparatus 10. Finally, the open area of the first and/or second valves 42, 50 in their opened configuration may be predetermined to provide a desired flow rate therethrough.

In an alternative embodiment, the leg 22 of the housing 12 may be omitted, and a valve (not shown) may be provided across the lateral opening 24 in a manner that is substantially coextensive with the wall of the housing 12. For example, a flapper valve may be provided that includes a hinge adjacent the second end 14 of the housing 12. When the lumen 18 is subjected to a vacuum, e.g., during exhalation, the flapper valve may open, thereby pulling air into the lateral opening 24 from the second branch 96. When the lumen 18 is subjected to a positive pressure, e.g., during inhalation, the flapper valve may be pushed coextensive with the lateral opening 24, i.e., closed, to substantially seal the lateral opening 24. This embodiment may minimize a delivery profile of the apparatus 10 during delivery and/or may eliminate the need to extend anything into the second branch 96 during deployment of the apparatus.

Accordingly, an apparatus in accordance with the present invention may control air flow during inhalation and/or exhalation, e.g., to maximize delivery of oxygen to a healthy region of the lung where it may be absorbed more effectively into the patient's blood. Because air flow into the isolated region is limited, oxygen-rich air may not be delivered substantially to the isolated region, which may not effectively transfer the oxygen to the patient's blood. In addition, limiting air flow into the isolated region may minimize over-expansion of the lung, which may facilitate effective breathing by the patient.

Further, during exhalation, because of the nozzle, a vacuum may be generated that may draw any residual air or carbon dioxide from the isolated region of the lung, which may help at least partially collapse the isolated region. This may also reduce the risk of over-expansion of the lung within the chest cavity, and make breathing easier for the patient.

In an alternative embodiment, a lung assist apparatus may be provided that may include separate components that may be implanted independently from one another (not shown). For example, a tubular housing or other support structure may be provided that may be compressed to a collapsed condition to facilitate delivery, e.g., using an apparatus similar to that shown in FIG. 3. The housing may be introduced and expanded within the bifurcation, similar to the housing 12 shown in FIGS. 4A-4C.

Once the housing is implanted, a nozzle may be introduced that may be secured within the housing (not shown). The nozzle and/or the housing may include struts and mating connectors for securing the nozzle within the housing. The first valve may be attached to the housing or the nozzle, and/or may be independently implanted, e.g., across the outer lumen 40 shown in FIGS. 4A-4C. The second valve may be coextensive with the housing, similar to the flapper valve described above, may be implanted within a leg of the housing, or may be implanted directly within the second branch, e.g., distally to the bifurcation. Operation of this alternative embodiment may proceed substantially similarly to the apparatus 10 described above.

In a alternative embodiments, a lung-assist device may be implanted within a branch including more than two branches communicating with a main passage, e.g., a trifurcation. In one embodiment, a first branch, e.g., communicating with a healthier region, may be used to draw air from second and third (or optionally more) branches, e.g., using the nozzle to generate a vacuum at lateral openings communicating with the second and third (or more) branches. Alternatively, multiple nozzles may be implanted that extend from first and second branches (communicating with healthier regions of a lung), that may include outlets disposed adjacent a third branch (communicating with a region to be isolated) such that both nozzles may generate a vacuum in the third branch.

Figure 6A:
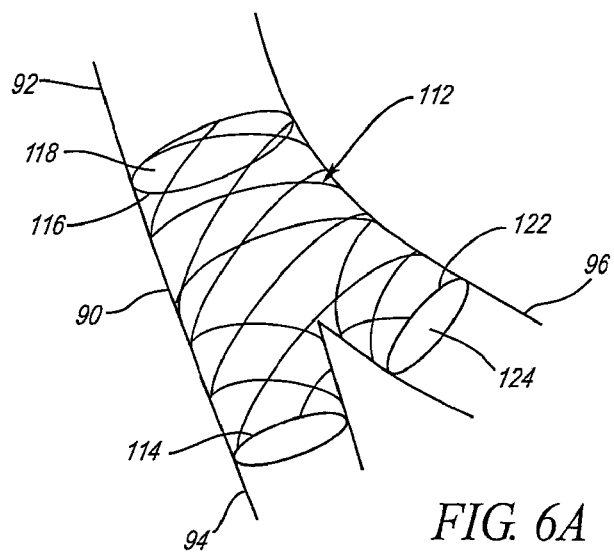
FIGS. 6A-6C are cross-sectional views of a bifurcation within a lung, showing a method for implanting another embodiment of a lung assist apparatus, in accordance with the present invention.
Figure 6B:
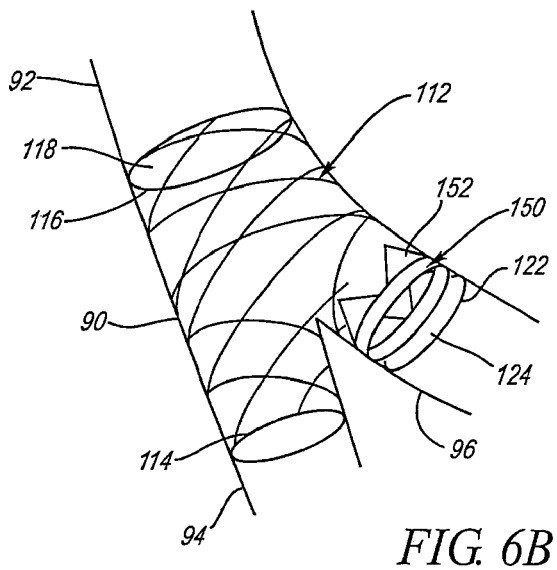
Figure 6C:
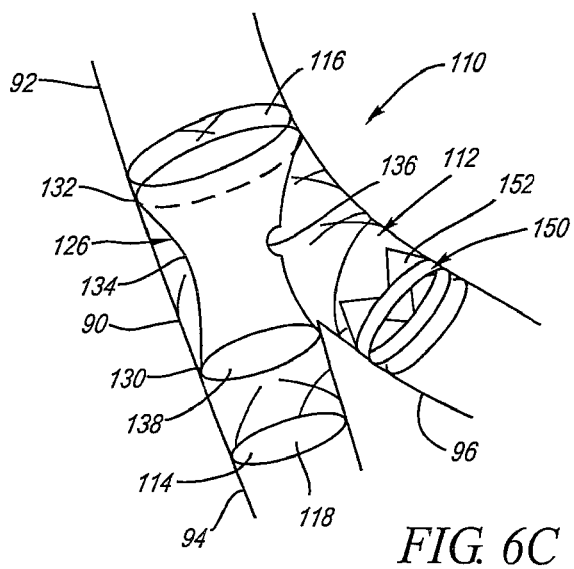

Turning to FIGS. 6A-6C, another embodiment of an apparatus 110 is shown that includes a support structure 112, a tubular venturi member 126, and a valve 150. The support structure 112 is a tubular mesh, including a first end 114, a second end 116, and a leg 122 extending laterally from between the first and second ends 114, 116. The support structure 112 defines a lumen 118 extending between the first and second ends 114, 116, and the leg 122 defines a lateral opening 124 communicating with the lumen 118.

The support structure 112 may be formed from an elastic, superelastic, and/or shape memory material, e.g., Nitinol, such that the support structure 112 may be compressed to a contracted condition (not shown) for facilitating delivery. The support structure 112 may be resiliently expandable towards an enlarged condition (best seen in FIG. 6A) due to its inherent elasticity and/or shape memory. Alternatively, the support structure 112 may be formed from a plastically deformable material, e.g., stainless steel, that may be crimped onto a balloon catheter or other device (not shown) and deformed towards the enlarged condition by expanding an underlying balloon or other expandable element (also not shown). In addition, the support structure 112 may include tissue-engaging elements, e.g., barbs, or an adhesive for further enhancing anchoring the support structure 112 within a branch 90.

The venturi member 126 includes a first end 130 and a second end 132 that are substantially larger than an intermediate region 134. For example, the venturi member 126 may have a cross-section that tapers from the first and second ends 130, 132 inwards towards the intermediate region or neck 134. An opening 136 may be provided in a wall at the intermediate region 134 of the venturi member 126 that communicates with a lumen 138 therein. The ends 130, 132 of the venturi member 126 may compressible to facilitate insertion, or may be of sufficient size to be inserted into a branch 90 while remaining fully expanded.

The valve 150 may be provided within or proximate the leg 122 to limit or otherwise control flow through the lateral opening 124. For example, the valve 50 may include a plurality of leaflets 152 that open to allow air flow into the lateral opening 124 (towards the second end 116 of the support structure 112), while limiting flow out of the lateral opening 124. Preferably, the leaflets 152 close to seal and prevent substantial air flow out of the lateral opening 124, as described further below.

To implant the apparatus 110, the support structure 112 may be delivered into a branch 90, such as a bifurcation within a lung, as shown in FIG. 6A, similar to the embodiment described above. The support structure 112 may be carried by a delivery device in its contracted condition until positioned across the branch 90, and then expanded to its enlarged condition. The first end 114 may be secured within a first branch 94, preferably communicating with a relatively healthy region of the lung (not shown), while the second end 116 is secured within a main passage 92, preferably communicating with a trachea (also not shown). The leg 122 may be disposed within a second branch 96, preferably communicating with a relatively diseased region of the lung, or other region that is to be isolated.

For example, the support structure 112 may be constrained to a catheter or other delivery device, e.g., by an overlying sheath (not shown), and released within the branch 90, whereupon the support structure 112 may automatically expand to substantially secure itself to tissue surrounding the branch 90. Alternatively or in addition, the support structure 112 may be expanded and substantially engaged with the surrounding tissue using an underlying expandable device, e.g., a balloon, which may be provided on the delivery device or may be introduced subsequent to releasing the support structure 112 within the branch 90. In alternative embodiments, the support structure 112 may be further anchored within the branch 90 by protruding barbs and/or an adhesive (not shown).

With the support structure 112 secured within the branch 90, the valve 150 may be delivered into the second branch 96, e.g., through the lumen 118 of the support structure 112, as shown in FIG. 6B. This may require compression of the valve 150, and so the valve 150 may be formed from an elastic or superelastic material. The valve 150 may be expanded independently within the second branch 96 or may be secured to the leg 122 of the support structure 112. Alternatively, the valve 150 may be delivered before delivering the support structure 112, e.g., into the second branch 96 beyond the location for the leg 122. In a further alternative, the valve 150 may be provided as part of the leg 122, and delivered when the support structure 122 is implanted.

Finally, as shown in FIG. 6C, the venturi member 126 may be introduced into the branch 90, and secured within the branch 90 and/or to the support structure 112. For example, the first and second ends 130, 132 may be of sufficient size to substantially engage walls of the first branch 94 and main passage 92, respectively. The first and second ends 130, 132 may be compressed to facilitate introduction into the branch 90, and may then be released to resiliently expand (or may be otherwise expanded) to engage the first branch 94 and the main passage 92. Alternatively, the venturi member 126 and support structure 112 may include cooperating connectors for attaching the venturi member 126 to the support structure 112. In a further alternative, an adhesive may be used to attach the venturi member 126 within the branch 90.

Once the apparatus 110 is implanted, it may provide assistance in evacuating and/or collapsing a diseased region or other region of the lung to be isolated. During inhalation, the valve 150 may close, thereby causing any air entering the branch 90 from the main passage 92 to pass through the lumen 138 of the venturi member 126 and into the first branch 94. Thus, incoming oxygen may be delivered to a healthy region of the lung where it may be absorbed into the patient's blood. During exhalation, air entering the branch 90 from the first branch 94, i.e., from the healthy region of the lung, passes through the lumen 138 of the venturi member 126 and into the main passage 92. Because of the narrow intermediate region 134, a vacuum may be created at the opening 136, thereby drawing air from the second branch 96. Because of the vacuum, the valve 150 may open, allowing any air within the diseased region of the lung to be removed via the main passage 96.

Apparatus and methods according to the present invention may be used alone or in combination with other procedures for reducing the volume of a lung. It may also be desirable to use the apparatus and methods of the present invention to assist flow of air or other fluids through branches of other systems within a patient, e.g., within the cardiovascular system.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A lung assist device comprising:
   a venturi tube having a first proximal end adapted to be coupled to a main branch of a lung and a second distal end adapted to be coupled to a first branch of a lung which communicates with the main branch, said venturi tube having an aperture in the wall thereof, which aperture is adapted to be located proximate to the opening of a second branch of the lung, which opening communicates with said main branch, said venturi having a neck between said first end and said second end and said aperture being located in the region of said neck, and
   a support structure for said venturi tube, said support structure having a tubular body which is coupled to said venturi tube in at least partially surrounding relationship to said venturi tube.

2. The device of claim 1 wherein said support structure comprises a bifurcated tubular body comprising a main tube which houses the venturi tube and a side tube which has a proximal end communicating with said aperture and a distal end extending away from said main tube.

3. The device of claim 2 wherein said side tube has a valve therein, which valve permits air flow toward said first proximal end of said venturi tube, but limits air flow through the distal end of said side tube.

* * * * *